(12) United States Patent
Holmes et al.

(10) Patent No.: US 8,834,511 B2
(45) Date of Patent: Sep. 16, 2014

(54) EXTERNAL NASAL DILATOR AND METHODS OF MANUFACTURE

(75) Inventors: Randel B. Holmes, Knoxville, TN (US); Dennis White, Knoxville, TN (US)

(73) Assignee: GlaxoSmithKline, LLC, Wilmington, DE (US)

( * ) Notice: Subject to any disclaimer, the term of this patent is extended or adjusted under 35 U.S.C. 154(b) by 252 days.

(21) Appl. No.: 12/941,222

(22) Filed: Nov. 8, 2010

(65) Prior Publication Data

US 2011/0054517 A1    Mar. 3, 2011

Related U.S. Application Data

(63) Continuation of application No. 11/620,892, filed on Jan. 8, 2007, now abandoned.

(60) Provisional application No. 60/862,548, filed on Oct. 23, 2006.

(51) Int. Cl.
*A61M 29/00* (2006.01)
*A61F 5/08* (2006.01)

(52) U.S. Cl.
CPC ........................................ *A61F 5/08* (2013.01)
USPC ...................... 606/199; 128/200.24

(58) Field of Classification Search
USPC ...................... 606/199; 128/200.24
See application file for complete search history.

(56) References Cited

U.S. PATENT DOCUMENTS

| | | |
|---|---|---|
| 3,906,073 A | 9/1975 | Kim |
| 4,075,379 A | 2/1978 | Lloyd |
| 4,101,358 A | 7/1978 | Kim |
| 4,422,650 A | 12/1983 | Reinsma et al. |
| 4,576,168 A | 3/1986 | Jalowayski |
| 4,693,858 A | 9/1987 | Volke |
| 4,743,499 A | 5/1988 | Volke |
| 4,827,925 A | 5/1989 | Vilasi |
| 4,942,714 A | 7/1990 | Langley, Jr. et al. |
| 5,022,389 A | 6/1991 | Brennan |
| 5,090,408 A | 2/1992 | Spofford et al. |

(Continued)

FOREIGN PATENT DOCUMENTS

| | | |
|---|---|---|
| EP | 0909151 | 10/1997 |
| EP | 0 820 744 A2 | 1/1998 |

(Continued)

OTHER PUBLICATIONS

U.S. Appl. No. 11/848,132, filed Aug. 2007, Smith.

*Primary Examiner* — Victor Nguyen
*Assistant Examiner* — Kevin Everage
(74) *Attorney, Agent, or Firm* — Joshua C. Sanders; Theodore R. Furman

(57) ABSTRACT

The present invention relates to external devices for dilating nasal passageways and to the manufacture thereof. More specifically, the external nasal dilator of the present invention usually comprises a resilient sheet, an adhesive layer, and an adhesive-protecting sheet. In some embodiments of the external nasal dilator, the resilient sheet defines a groove for reducing the peel force that results from bending the dilator over the bridge of the nose. In addition to the groove or in lieu thereof, some embodiments of the external nasal dilator comprise a nasal passage region having a reduced width to reduce the peel force. Finally, the dilator can comprise a sheet of adhesive tape, which in some embodiments can provide an instant tack surface to facilitate application of the dilator.

7 Claims, 11 Drawing Sheets

(56) References Cited

U.S. PATENT DOCUMENTS

| | | | |
|---|---|---|---|
| 5,186,168 A | 2/1993 | Spofford et al. | |
| 5,269,769 A | 12/1993 | Dhara et al. | |
| 5,297,546 A | 3/1994 | Spofford et al. | |
| 5,303,917 A | 4/1994 | Uke | |
| 5,392,568 A | 2/1995 | Howard, Jr. et al. | |
| 5,466,724 A | 11/1995 | Volke et al. | |
| 5,476,091 A | 12/1995 | Johnson | |
| 5,530,989 A | 7/1996 | Remmert et al. | |
| 5,533,499 A | 7/1996 | Johnson | |
| 5,533,503 A | 7/1996 | Doubek et al. | |
| 5,534,561 A | 7/1996 | Volke | |
| 5,549,103 A | 8/1996 | Johnson | |
| 5,569,218 A | 10/1996 | Berg | |
| 5,605,543 A | 2/1997 | Swanson | |
| 5,611,333 A * | 3/1997 | Johnson | 128/200.24 |
| 5,653,224 A | 8/1997 | Johnson | |
| 5,706,800 A | 1/1998 | Cronk et al. | |
| 5,743,876 A | 4/1998 | Swanson | |
| 5,746,770 A | 5/1998 | Zeitels et al. | |
| 5,890,486 A | 4/1999 | Mitra et al. | |
| 5,897,537 A | 4/1999 | Berg et al. | |
| 5,911,715 A | 6/1999 | Berg et al. | |
| 5,957,126 A | 9/1999 | Neeser | |
| 6,029,658 A | 2/2000 | De Voss | |
| 6,196,228 B1 | 3/2001 | Kreitzer et al. | |
| 6,213,121 B1 | 4/2001 | Cardarelli | |
| 6,228,101 B1 | 5/2001 | Stratton | |
| 6,244,265 B1 | 6/2001 | Cronk et al. | |
| 6,248,247 B1 | 6/2001 | Goenka et al. | |
| 6,270,831 B2 | 8/2001 | Kumar et al. | |
| 6,276,360 B1 | 8/2001 | Cronk et al. | |
| 6,318,362 B1 | 11/2001 | Johnson | |
| 6,357,436 B1 | 3/2002 | Kreitzer et al. | |
| 6,453,901 B1 | 9/2002 | Ierulli et al. | |
| 6,463,633 B1 | 10/2002 | Sangani et al. | |
| 6,475,703 B2 | 11/2002 | Li et al. | |
| 6,550,474 B1 | 4/2003 | Anderson et al. | |
| 6,569,934 B2 | 5/2003 | Noel, III | |
| 6,631,714 B2 * | 10/2003 | Von Duyke et al. | 128/200.24 |
| 6,645,338 B1 | 11/2003 | Sangani et al. | |
| 6,678,553 B2 | 1/2004 | Lerner et al. | |
| 6,767,202 B2 | 7/2004 | Gorman et al. | |
| 6,769,428 B2 | 8/2004 | Cronk et al. | |
| 6,769,429 B1 | 8/2004 | Benetti | |
| 6,858,024 B1 | 2/2005 | Berg et al. | |
| 6,902,575 B2 | 6/2005 | Laakso et al. | |
| 6,969,479 B2 | 11/2005 | Gorman et al. | |
| 7,011,093 B2 | 3/2006 | Anderson et al. | |
| 7,013,889 B2 | 3/2006 | Cronk et al. | |
| 7,017,580 B2 | 3/2006 | Prescott et al. | |
| 7,037,457 B2 | 5/2006 | Seidel et al. | |
| 7,114,495 B2 | 10/2006 | Lockwood, Jr. | |
| 2001/0002000 A1 | 5/2001 | Kumar et al. | |
| 2002/0000227 A1 | 1/2002 | Duyke et al. | |
| 2002/0086243 A1 | 7/2002 | Li et al. | |
| 2003/0114910 A1 | 6/2003 | Juhani Laakso et al. | |
| 2004/0005830 A1 | 1/2004 | Anderson et al. | |
| 2004/0149290 A1 | 8/2004 | Nelson et al. | |
| 2004/0231679 A1 | 11/2004 | Prescott et al. | |
| 2004/0242976 A1 | 12/2004 | Abreu | |
| 2004/0243102 A1 | 12/2004 | Berg et al. | |
| 2005/0045188 A1 | 3/2005 | Mendius et al. | |
| 2005/0081846 A1 | 4/2005 | Barney | |
| 2005/0081857 A1 | 4/2005 | Fenton | |
| 2005/0124445 A1 | 6/2005 | Veilleux et al. | |
| 2005/0129913 A1 | 6/2005 | Kobayashi et al. | |
| 2005/0149080 A1 | 7/2005 | Hunter et al. | |
| 2005/0149158 A1 | 7/2005 | Hunter et al. | |
| 2005/0161046 A1 | 7/2005 | Michaels | |
| 2005/0165488 A1 | 7/2005 | Hunter et al. | |
| 2005/0175663 A1 | 8/2005 | Hunter et al. | |
| 2005/0175665 A1 | 8/2005 | Hunter et al. | |
| 2005/0175703 A1 | 8/2005 | Hunter et al. | |
| 2005/0177225 A1 | 8/2005 | Hunter et al. | |
| 2005/0178395 A1 | 8/2005 | Hunter et al. | |
| 2005/0178396 A1 | 8/2005 | Hunter et al. | |
| 2005/0181008 A1 | 8/2005 | Hunter et al. | |
| 2005/0181011 A1 | 8/2005 | Hunter et al. | |
| 2005/0189372 A1 | 9/2005 | Fenton | |
| 2005/0244614 A1 | 11/2005 | Bharadwaj | |
| 2005/0284485 A9 | 12/2005 | Nelson et al. | |
| 2006/0000472 A1 | 1/2006 | Fenton | |
| 2006/0085027 A1 | 4/2006 | Santin et al. | |
| 2006/0112958 A1 | 6/2006 | Fisher et al. | |
| 2008/0058858 A1 | 3/2008 | Smith | |

FOREIGN PATENT DOCUMENTS

| | | |
|---|---|---|
| EP | 0 861 674 A1 | 9/1998 |
| EP | 0 799 114 B1 | 10/1998 |
| EP | 0 912 210 B1 | 9/2003 |
| EP | 0 820 743 B1 | 4/2004 |
| EP | 0 820 745 B1 | 4/2004 |
| EP | 1 006 963 B1 | 4/2004 |
| EP | 0 900 553 B1 | 11/2004 |
| EP | 1 299 056 B1 | 3/2006 |
| EP | 1 267 976 B1 | 6/2006 |
| ES | 289561 | 10/1985 |
| WO | WO92/22340 | 12/1992 |
| WO | WO93/24161 | 12/1993 |
| WO | EP 0 659 522 A1 | 6/1995 |
| WO | WO95/21640 | 8/1995 |
| WO | WO95/24236 | 9/1995 |
| WO | WO97/38651 | 10/1997 |
| WO | WO97/46275 | 12/1997 |
| WO | WO98/27897 | 7/1998 |
| WO | WO99/27880 | 6/1999 |
| WO | EP 0 588 949 B1 | 7/1999 |
| WO | WO99/36193 | 7/1999 |
| WO | EP 1 006 764 A2 | 6/2000 |
| WO | WO01/74432 A1 | 10/2001 |
| WO | WO01/96457 | 12/2001 |
| WO | EP 1 174 100 A2 | 1/2002 |
| WO | WO02/05734 A2 | 1/2002 |
| WO | WO02/15896 A2 | 2/2002 |
| WO | WO03/051235 A1 | 6/2003 |
| WO | WO03/060843 A1 | 7/2003 |
| WO | WO2005/051292 | 6/2005 |
| WO | WO2005/063328 | 7/2005 |

* cited by examiner

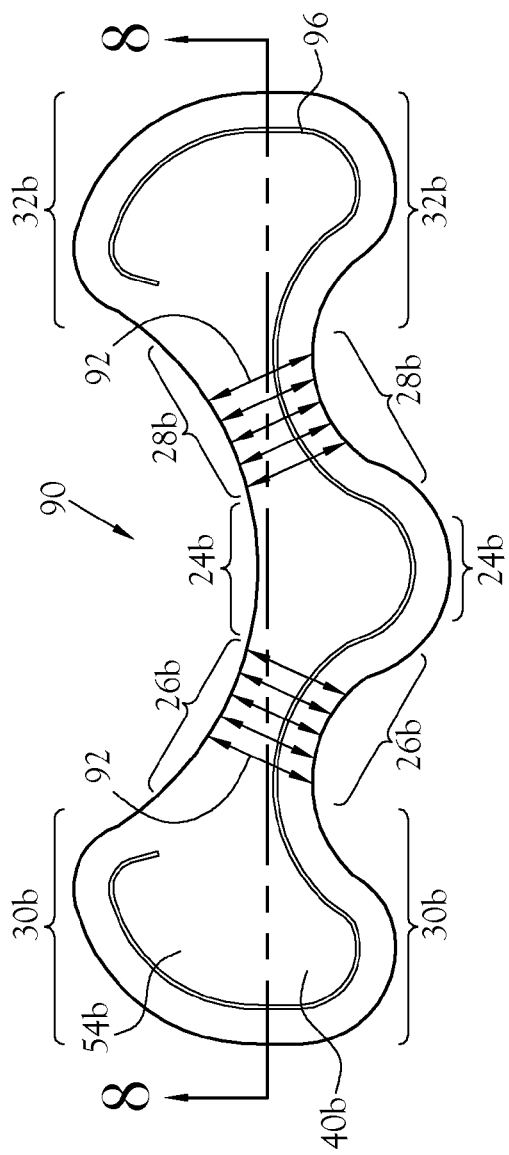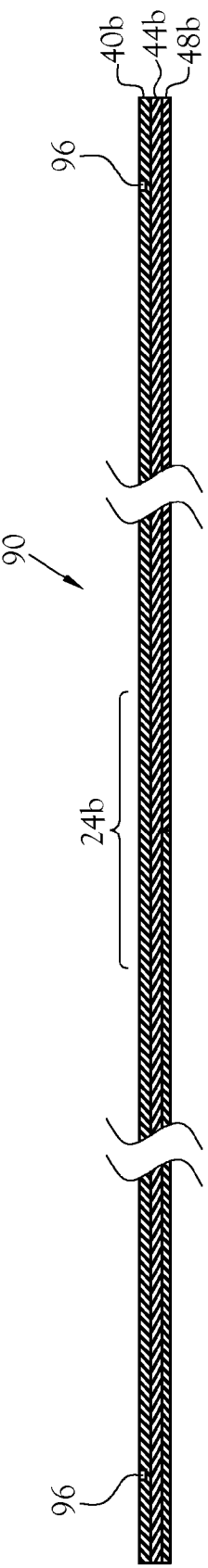

EXTERNAL NASAL DILATOR AND METHODS OF MANUFACTURE

CROSS-REFERENCE TO RELATED APPLICATIONS

This application is a continuation of U.S. application Ser. No. 11/620,892 filed Jan. 8, 2007 now abandoned which claims the benefit of U.S. Provisional Application No. 60/862,548 filed Oct. 23, 2006.

STATEMENT REGARDING FEDERALLY-SPONSORED RESEARCH OR DEVELOPMENT

Not Applicable

BACKGROUND OF THE INVENTION

Field of Invention

The invention relates to external devices for dilating nasal passageways and to the manufacture thereof.

BRIEF SUMMARY OF THE INVENTION

The external nasal dilator of the present invention generally comprises a resilient sheet, an adhesive layer, and an adhesive-protecting sheet. Some embodiments also include a sheet of adhesive tape. The resilient sheet is superposed on the adhesive layer, and the adhesive layer is superposed on the adhesive-protecting sheet, which is removably adhered to the adhesive layer. In those embodiments that comprise the sheet of adhesive tape, it is superposed and adhered to the resilient sheet.

The resilient sheet comprises a resilient thermoplastic material (e.g., PET, boPET, PETG, HDPE, and polyester). Generally, (1) the adhesive layer comprises a hydrocolloid and (2) the adhesive-protecting sheet comprises polypropylene, a similar thermoplastic resin, or a paper-based material. In at least some embodiments, the resilient sheet defines at least one groove for reducing the peel force that results from bending the dilator (namely, the resilient sheet) over the bridge of the nose. Either or both major surfaces of the resilient sheet can define a groove. In addition to the groove or in lieu thereof, some embodiments of the external nasal dilator comprise a nasal passage region having a reduced width. This serves to reduce the peel force, including any peel force that originates from the bridge region of the external nasal dilator. Finally, in some of the embodiments of the dilator that include the sheet of adhesive tape, the resilient sheet and the adhesive layer each have a lesser area than the sheet of adhesive tape. Thus, when the sheet of adhesive tape is superposed on (and adhered to) the resilient sheet, which in turn is superposed on the adhesive layer, some of the adhesive surface of the adhesive tape still is available to adhere to the nose upon application (which follows removal of the adhesive-protecting sheet). Generally, the adhesive tape comprises an acrylic adhesive, which is fast-acting. Thus, these available adhesive surfaces function as an "instant tack surfaces," thereby facilitating application of the dilator.

The present invention also includes various methods of making the external nasal dilator. At least some of the embodiments of the external nasal dilator disclosed herein are amenable to continuous and automated manufacture. For example, in one embodiment of the method, a roll of a three-layered material is used as the starting material, the three layers consisting substantially and respectively of (1) a resilient sheet, (2) an adhesive-protecting sheet, and (3) an adhesive layer between the resilient sheet and the adhesive-protecting sheet. A series of dies are used to cut the three-layered material into the appropriate shape and (when necessary) to impress grooves in the resilient sheet.

BRIEF DESCRIPTION OF THE SEVERAL VIEWS OF THE DRAWINGS

The above-mentioned features of the invention will become more clearly understood from the following detailed description of the invention read together with the drawings in which:

FIG. 7 is a top plan view of an embodiment of the external nasal dilator comprising (1) "choked down" nasal passage regions and (2) a peripheral groove;

FIG. 8 is an enlarged cross-sectional view of the external nasal dilator taken along lines 8-8 of FIG. 7;

DETAILED DESCRIPTION OF THE INVENTION

Figure 1:
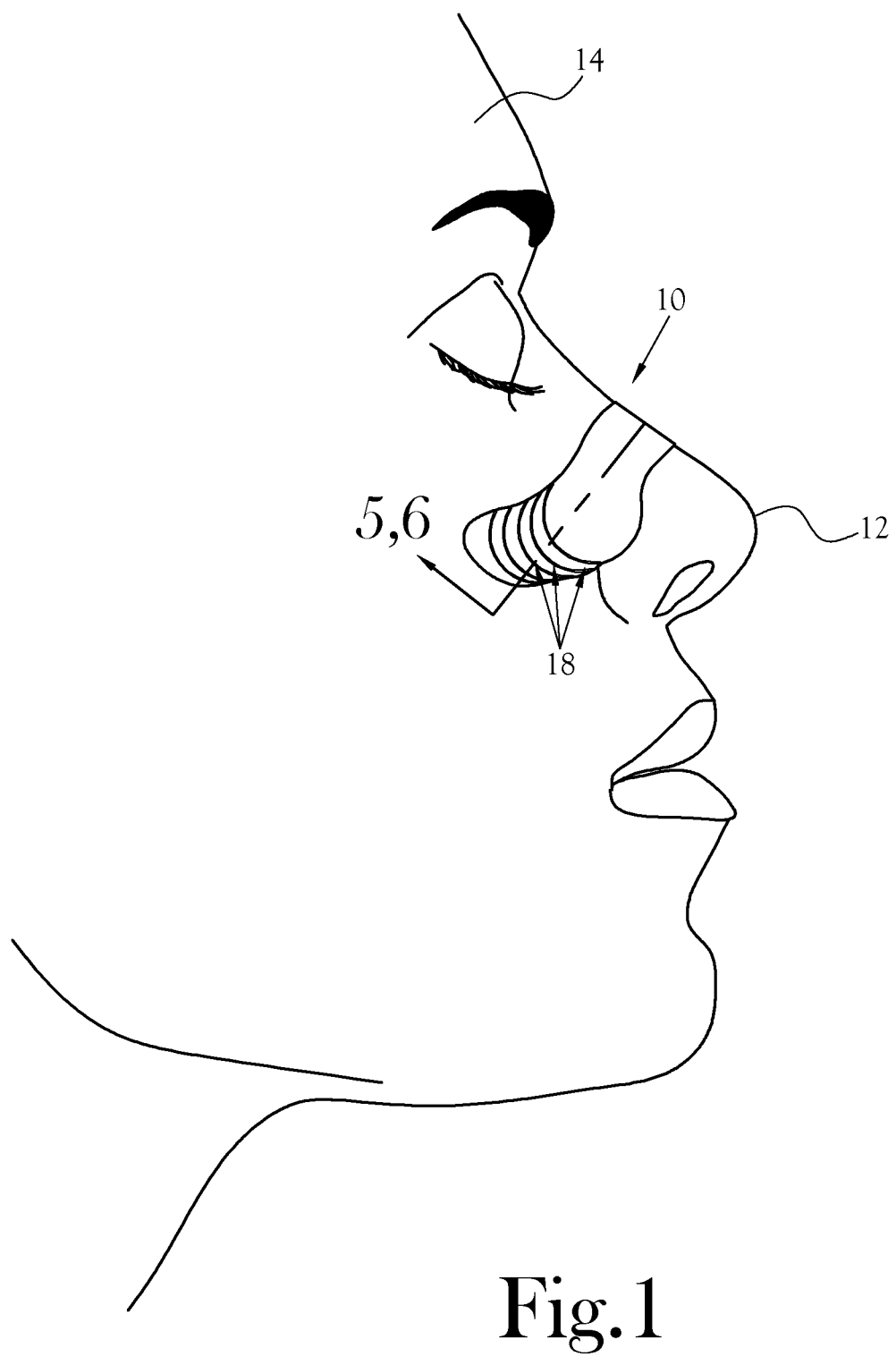
FIG. 1 is a perspective view of an embodiment of the external nasal dilator of the present invention adhered to a person's nose.

The present invention, i.e., the external nasal dilator and methods of manufacture, is described more fully hereinafter. From the outset, it is worth noting that this invention may be embodied in many different forms and should not be construed as limited to the specific embodiments described herein. Rather, the embodiments described herein are provided to ensure that this description is thorough and complete, and to ensure that the scope of the invention is communicated effectively to those skilled in the art. It is also worth noting that the Figures are provided merely as a guide to assist those skilled in the art in understanding and appreciating the scope of the invention. Finally, the disclosure provided in U.S. Provisional Application No. 60/862,548, filed Oct. 23, 2006, is incorporated by reference.

DEFINITIONS

"Adhesive tape" means tape coated on one side with an adhesive substance.

"Border" means the line or relatively narrow space that marks the outer limit of something.

"Etch" means to produce (as a pattern or design) on a hard material by eating into the material's surface (as by acid or laser beam).

"Nonwoven" means made of fibers held together by interlocking or bonding (as by chemical or thermal means); not woven, knitted, or felted.

"Paper" means a felted or matted sheet of cellulose fibers formed on a fine-wire screen from a dilute water suspension, and bonded together as the water is removed and the sheet is dried.

"Peeling" means to pull a layer of material away from another layer, especially by breaking approximately one row of bonds at a time.

"Peel force" is the force required to separate by peeling two layers of pliable material that have been adhered together. The peel force measured is not merely an inherent property of the adhesive, but depends on many variables, such as the test method, temperature, peel rate, degree of contact, adhesive chemistry and thickness, aging, adhesive backing, and the substrate. Common peel tests include the T-peel test, the 180° peel test, and the 90° peel test.

"Polyethylene terephthalate" is a thermoplastic polyester resin made from ethylene glycol and terephthalic acid. Abbreviated PETG.

"Resilience" is the capability of a strained body to recover its size and shape following deformation.

"Resilient" means characterized or marked by resilience; implies the ability to recover shape quickly when the deforming force or pressure is removed.

"Shearing stress" is a stress in which the material on one side of a surface pushes on the material on the other side of the surface with a force that is parallel to the surface. Also known as shear stress; tangential stress.

"Thermoplastic resin" is a material with a linear macromolecular structure that will repeatedly soften when heated and harden when cooled; for example, styrene, acrylics, cellulosics, polyethylenes, vinyls, nylons, and fluorocarbons.

Other words and terms are defined as necessary in the detailed description that follows.

External Nasal Dilator and Methods of Manufacture

External nasal dilators, which generally are secured to the skin of the nose by an adhesive, lift the outer wall tissues of the nostrils, thereby dilating the nasal passages. Such dilators reduce the resistance to airflow during breathing, especially inhalation. FIG. 1 shows an embodiment 10 of the external nasal dilator ("dilator") of the present invention adhered to the nose 12 of the wearer 14. The dilator 10 defines grooves 18, the significance of which is explained later in this specification.

Figure 2:
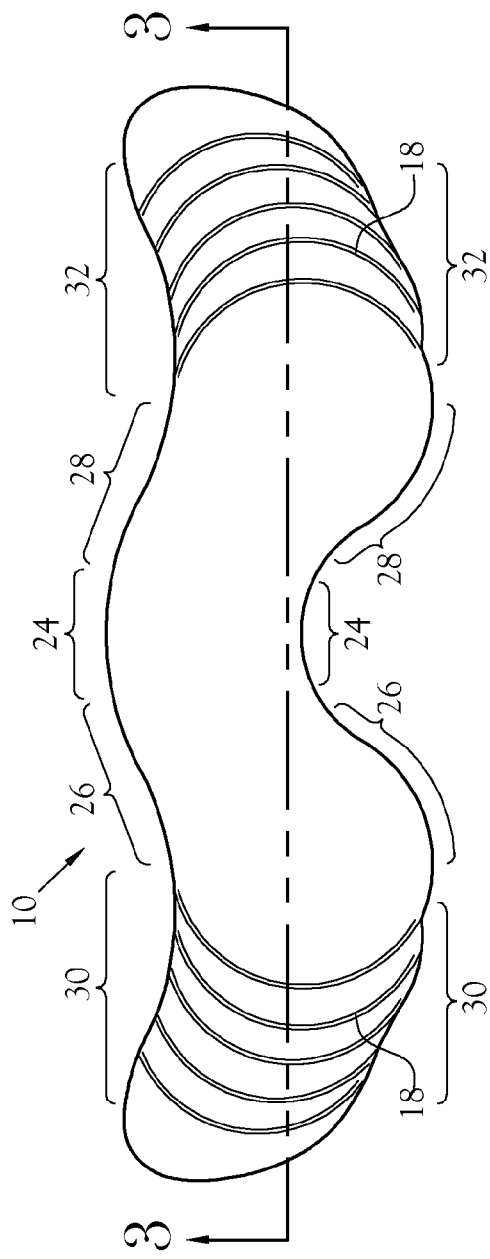
FIG. 2 is a top plan view of the embodiment of the external nasal dilator shown in FIG. 1.

FIG. 2 is a top plan view of the embodiment 10 in its planar state, i.e., prior to application. The embodiment 10 has a bridge region 24, which is for engaging the bridge of the wearer's nose, and it 10 also has a first nasal passage region 26 and a second nasal passage region 28. The first nasal passage region 26 is for engaging the nasal tissue that comprises the outer wall (not shown) of the first nasal passage (not shown), and the second nasal passage region 28 is for engaging the nasal tissue that comprises the outer wall (not shown) of the second nasal passage (not shown). Additionally, the embodiment 10 has a first end region 30 and a second end region 32.

Figure 3:
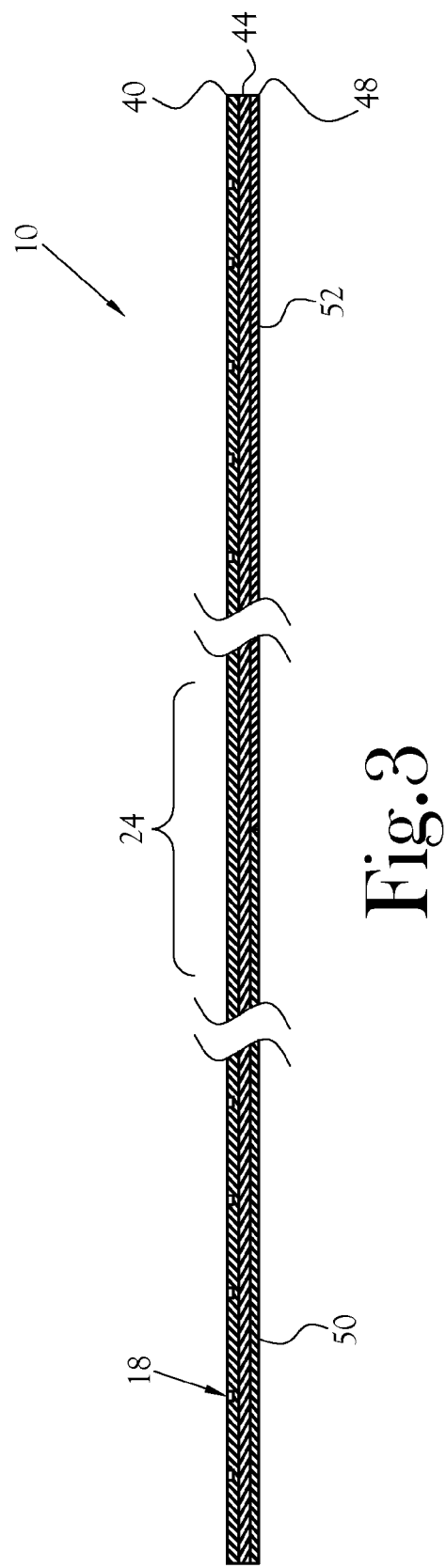
FIG. 3 is an enlarged cross-sectional view of the external nasal dilator taken along lines 3-3 of FIG. 2.

FIG. 3 is an enlarged cross-sectional view of the embodiment 10 taken along lines 3-3 of FIG. 2. The embodiment 10 has three (3) layers: a resilient sheet 40, an adhesive layer 44, and an adhesive-protecting sheet 48. The resilient sheet 40 has the grooves 18 introduced previously in FIG. 1, and is comprised of a resilient material, e.g., polyethylene terephthalate ("PET"), biaxially-oriented polyethylene terephthalate ("boPET"), polyethylene terephthalate glycol ("PETG"), high-density polyethylene ("HDPE"), and polyester. Additionally, other thermoplastic materials (e.g., thermoplastic resins) having similar properties may be suitable for use as the resilient sheet 40. The adhesive layer 44 generally comprises a hydrocolloid. Preferably, the adhesive layer 44 is pressure-sensitive (and/or heat-sensitive) and bio-compatible. Finally, the adhesive-protecting sheet 48 removably covers the adhesive layer 44, protecting it 44 until the embodiment 10 is applied to the wearer's nose. Generally, the adhesive-protecting sheet 48 is comprised of polypropylene, a similar thermoplastic resin, or a paper-based material. Preferably, and as shown in FIG. 3, the adhesive-protecting sheet 48 is divided equally along the latitudinal axis of the embodiment 10 into a first section 50 and a second section 52, to facilitate its 48 removal immediately prior to application.

Figure 4:
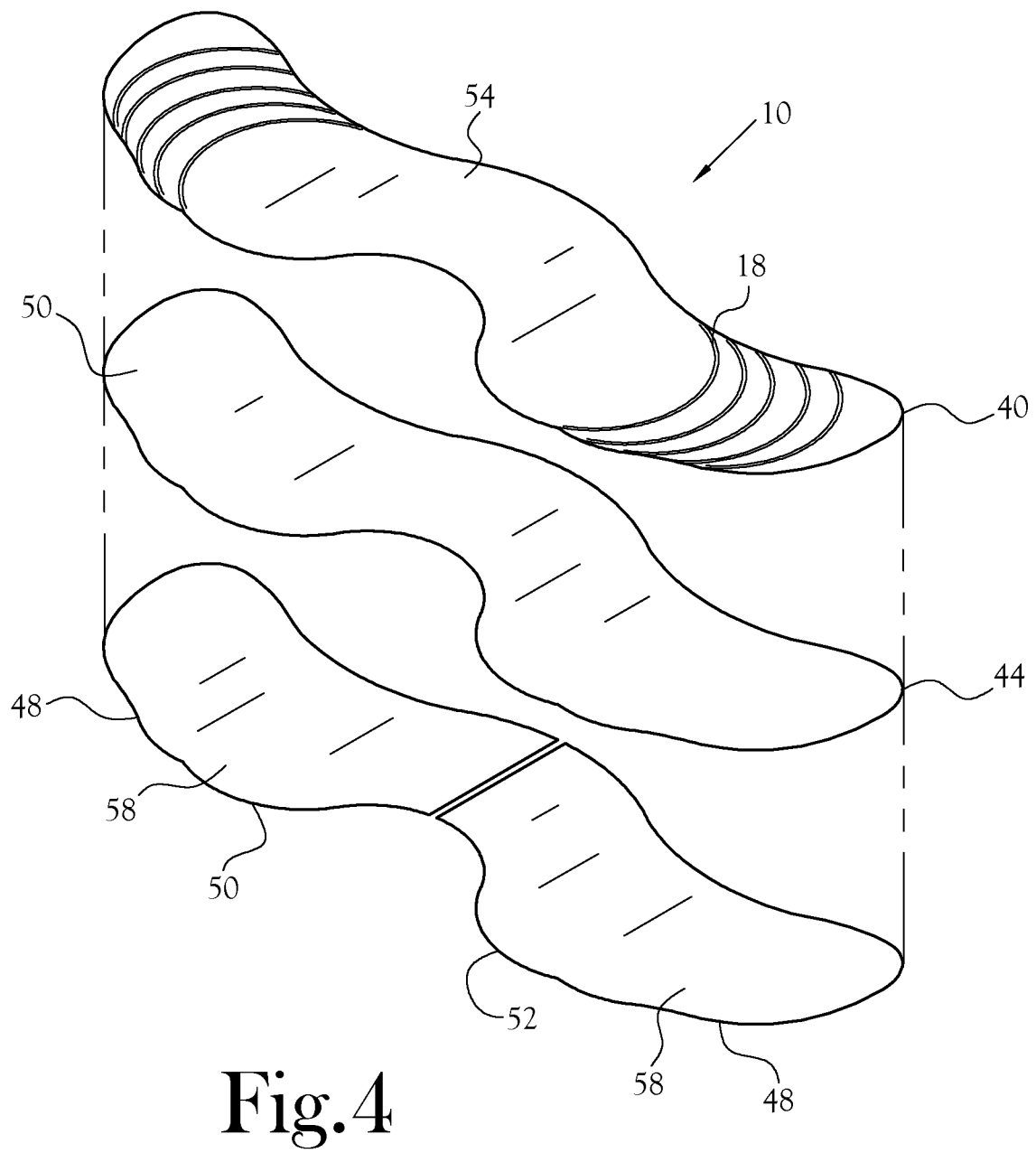
FIG. 4 is an exploded view of the embodiment of the external nasal dilator shown in FIGS. 1-3.

FIG. 4 is an exploded view of embodiment 10 in its planar state (i.e., prior to application) showing the resilient sheet 40, the adhesive layer 44, and the first section 50 and second section 52 of the adhesive-protecting sheet 48. The adhesive layer 44 defines two major surfaces: a first major surface 50 and a second major surface (not visible in FIG. 4), which is opposite thereto. Similarly, the resilient sheet 40 defines two major surfaces, which are referred to respectively as the third major surface 54 and the fourth major surface (not visible in FIG. 4), which is opposite thereto. Finally, the adhesive-protecting sheet 48 also defines two major surfaces, which are referred to respectively as the fifth major surface 58 and the sixth major surface (not visible in FIG. 4), which is opposite thereto. In an embodiment such as embodiment 10, the maximum thickness of the resilient sheet 40 generally ranges from approximately ten (10) millimeters to approximately fourteen (14) millimeters. The depth of the grooves 18 in the resilient sheet 40 can range from approximately seven (7) millimeters to approximately eleven (11) millimeters, depending on the maximum thickness of the resilient sheet 40. Generally, the minimum thickness of the resilient sheet 40, when measured from the base of a groove 18, ranges from approximately three (3) millimeters to approximately four (4) millimeters.

Figure 5:
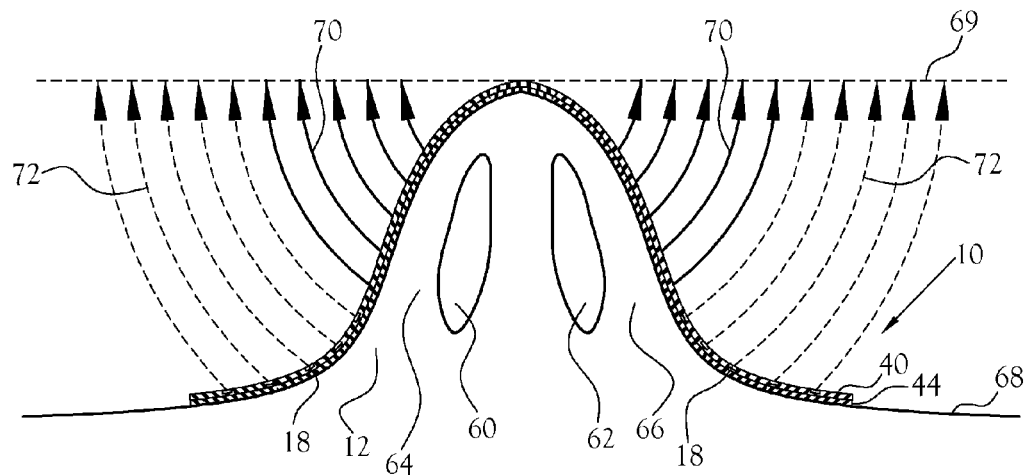
FIG. 5 is an enlarged cross-sectional view taken along lines 5-5 of FIG. 1.

FIG. 5 is an enlarged cross-sectional view of embodiment 10 taken along lines 5-5 of FIG. 1. FIG. 5 shows embodiment 10 following application to the nose 12. Additionally, FIG. 5 shows the first nasal passage 60 and the second nasal passage 62, as well as the outer wall of the first nasal passage 64 and the outer wall of the second nasal passage 66. The resilient sheet 40 and the adhesive layer 44 are shown also. Embodiment 10 is shown bent over the bridge of the nose and secured to the nose 12 by adhesion. More specifically, the resilient sheet 40 is adhered to the skin 68 of the nose 12 by the adhesive layer 44. The resilient sheet 40 opposes the adhesive forces because that layer 40, due to its resilience, seeks to recover its original planar state following the removal of the deforming force or pressure (e.g., bending force). Thus, the resilient sheet 40, in seeking to recover its original planar state (as represented by tangent line 69), exerts force via the adhesive layer 44 on the outer walls 64, 66 of the nasal passages 60, 62, causing them to dilate. This force, which is necessary to the functioning of the dilator, also doubles as a peel force. The peel force, which is represented by solid arrows 70 and dashed arrows 72, opposes the adhesive forces between the resilient sheet 40 and the adhesive layer 44 and between the adhesive layer 44 and the skin 68 of the nose 12. Accordingly, the peel force encourages the adhesive layer 44 to detach from the resilient sheet 40 and/or the skin 68. Such detachment, if extensive, can significantly impair the functioning of a dilator. In embodiment 10, however, the grooves 18 in the resilient sheet 40 (which were introduced previously) serve to reduce the magnitude of the peel forces in their proximity, without significantly compromising dilation. The grooves 18 therefore reduce the risk of detachment, promoting reliability of performance. Grooves such as those of embodiment 10 can be located in various regions of the resilient sheet 40 where at least some of the force therein that doubles as a peel force is unnecessary to sufficiently dilate the nasal passages. Grooves, when located therein, can serve to reduce that force without significantly compromising dilation. In FIG. 5, the dashed arrows 72 represent peel forces that would have had a greater magnitude but for the presence of the grooves in their proximity. In turn, arrows 70 represent peel forces that are not significantly affected by the grooves 18.

Figure 6:
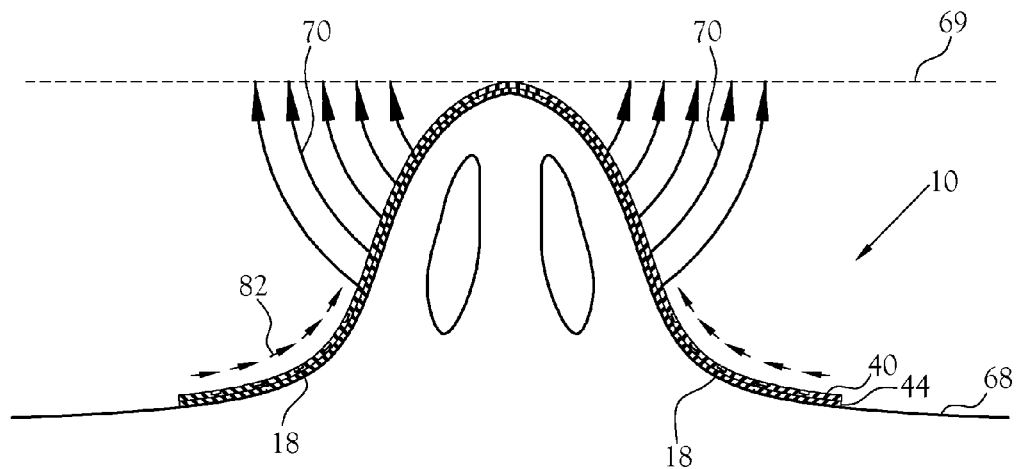
FIG. 6 is an enlarged cross-sectional view taken along lines 6-6 of FIG. 1.

FIG. 6 is an enlarged cross-sectional view of embodiment 10 taken along lines 6-6 of FIG. 1. Although the perspective of FIG. 6 is identical to that shown in FIG. 5, FIG. 6 does not include the dashed arrows 72, which represent the peel forces having a reduced magnitude. (The dashed arrows 72 have been omitted from FIG. 6 in the interest of clarity.) The reduction of some of the peel forces increases the significance of other forces that are substantially unaffected by the inclusion of the grooves 18, including forces derived from shearing stress (hereinafter referred to as "shear forces"). In FIG. 6, the shear forces that are proximate to the grooves 18 are represented by arrows 82. It is also worth noting that FIG. 6 has not been included for accurately disclosing the shear forces that are present in the proximity of the grooves 18. Rather, the arrows 82 have been included merely to assist in the understanding of the invention disclosed herein by those skilled in the art, who will recognize, for example, that shear forces may operate in either direction parallel to a surface. Although the shear forces have not been substantially reduced by the grooves 18, the resilient material (e.g., PET, boPET, and PETG) and the adhesive substance (e.g., hydrocolloid) that respectively comprise the resilient sheet 40 and the adhesive layer 44 of the dilator generally have greater tolerance for shear forces than for peel forces.

FIG. 7 a top plan view of another embodiment 90 of the present invention. FIG. 7 shows the embodiment 90 in its planar state, i.e., prior to application. Similar to embodiment 10, embodiment 90 has a bridge region 24*b*, a first nasal passage region 26*b*, a second nasal passage region 28*b*, a first end region 30*b*, and a second end region 32*b*. Relative to the nasal passage regions of embodiment 10, the nasal passage regions of embodiment 90 have a significantly shorter average width, as determined by measuring along lines 92. The nasal passage regions of embodiment 90 have been "choked down" to reduce peel forces, including the peel forces that result from the bending of the resilient sheet 40*b* over the bridge of the nose, at least some of which originate from the bridge region 24*b*. Additionally, as shown in FIG. 7, the third major surface 54*b* of the resilient sheet 40*b* defines a peripheral groove 96 for the purpose of reducing peel forces in its proximity. Finally, in some embodiments of the present invention, the surface areas of the first end region 30*b* and second end region 32*b* may be increased to accommodate a greater area of adhesive layer (not shown) in those regions 30*b*, 32*b*. This can at least partially compensate for the decreased surface area of adhesive layer in the nasal passage regions 26*b*, 28*b*, which have been "choked down."

FIG. 8 is an enlarged cross-sectional view of embodiment 90 taken along lines 8-8 of FIG. 7. FIG. 8 shows the resilient sheet 40*b*, the peripheral groove 96, the adhesive layer 44*b*, the adhesive-protecting sheet 48*b*, and the bridge region 24*b*.

Still other embodiments of the present invention have grooves in the other major surface ("fourth major surface") of the resilient sheet (i.e., the surface of the resilient sheet that is contacting the adhesive layer 44) either instead of, or in addition to, the grooves 18 on the third major surface 54 of the resilient sheet 40. Thus, the resilient sheet 40 can define grooves on either or both major surfaces, although it is preferable to have grooves on just one major surface. The grooves, themselves, may be straight or curved (e.g., arcuate), and they may be continuous or discontinuous. Indeed, many groove configurations are possible that are consistent with the scope of the present invention.

Figure 9A:
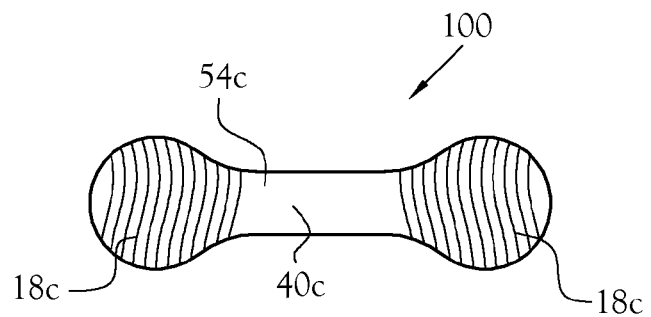
FIG. 9A is a top plan view of an embodiment of the external nasal dilator comprising (1) end regions that are rounded and flared and (2) curved grooves.
Figure 9B:
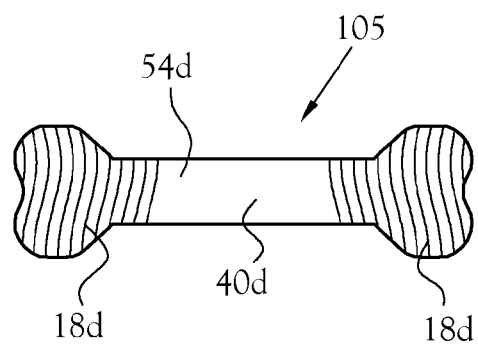
FIG. 9B is a top plan view of an embodiment of the external nasal dilator comprising curved grooves.
Figure 9C:
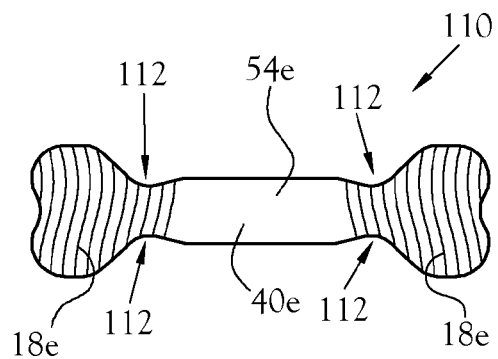
FIG. 9C is a top plan view of an embodiment of the external nasal dilator comprising "choked down" nasal passage regions and curved grooves.

FIGS. 9A, 9B, and 9C each show a top plan view of a different embodiment of the present invention. The external nasal dilator of the present invention can assume a variety of shapes, three more of which are illustrated in FIGS. 9A-9C, respectively. As in FIGS. 2 and 7, the resilient sheet 40 and any grooves defined on the first surface 16 of the resilient sheet 40 are visible. FIG. 9A shows an embodiment 100 of an external nasal dilator having rounded, flared ends. The resilient sheet 40*c* and the third surface 54*c* are depicted, as are the grooves 18*c* defined by the third surface 54*c*. FIG. 9B shows an embodiment 105 having an overall shape similar to that of a bone. Again, the resilient sheet 40*d* and the third surface 54*d* are depicted, as are the grooves 18*d* defined by the third surface 54*d*. Finally, FIG. 9C also shows an embodiment 110 having an overall shape similar to that of a bone. In this embodiment, however, the bone shape has been "choked down" to reduce peeling forces. The arrows 112 identify the location of the "choke down." Again, the resilient sheet 40*e* and the third surface 54*e* are depicted, as are the grooves 18*e* defined by the third surface 54*e*.

Figure 10:
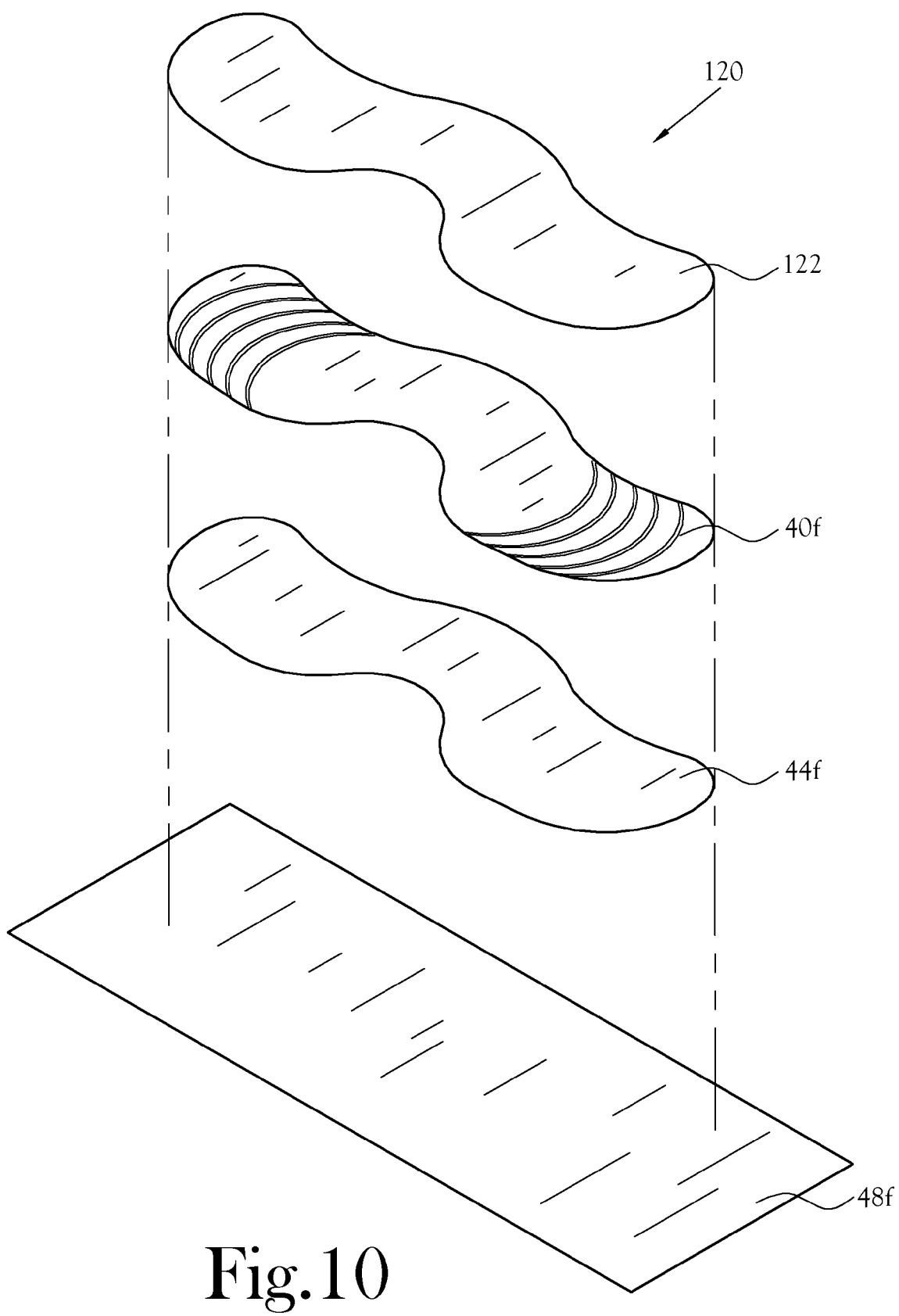
FIG. 10 is an exploded view of an embodiment of the external nasal dilator comprising an additional layer (i.e., sheet of adhesive tape)

Still other embodiments of the present invention include an additional (fourth) layer, specifically, a sheet of an adhesive tape. FIG. 10 is an exploded view of one of these embodiments 120 in its planar state (i.e., prior to application). As shown in FIG. 10, this embodiment 120 has four (4) layers: a sheet of adhesive tape 122; a resilient sheet 40*f*; an adhesive layer 44*f*; and an adhesive-protecting sheet 48*f*. The sheet of adhesive tape 122 is adhered to the resilient sheet 40*f*, which in turn is adhered to the adhesive-protecting sheet 48*f* via the adhesive layer 44*f*. Generally, the sheet of adhesive tape 122 is a nonwoven tape and includes an acrylic adhesive. However, the adhesive tape 122 can be woven tape or a film tape. In at least some of these embodiments, the sheet of adhesive tape 122 is less reflective than the resilient sheet 40*f*. Thus, by covering the resilient sheet 40*f*, the sheet of adhesive tape 122 may reduce reflections that cause glare, which generally is uncomfortable for the wearer. The three remaining layers (i.e., the resilient sheet 40*f*, the adhesive layer 44*f*, and the adhesive-protecting sheet 48*0*) are similar, respectively, to the corresponding layers of the embodiments 10, 90 described previously. In this embodiment 120, the sheet of adhesive tape 122, the resilient sheet 40*f*, and the adhesive layer 44*f* are all at least essentially congruent, i.e., at least nearly identical in size and shape. Nevertheless, the adhesive-protecting sheet 48f may have any shape and size, provided it 48f at least essentially covers the adhesive layer 44f, thereby protecting it 44f until the embodiment 120 is applied to the wearer's nose. It is also worth noting that, as shown in these previous embodiments 10, 90, the resilient sheet 40f may define grooves (not shown) for the purpose of reducing the magnitude of the peel forces in their proximity.

Figure 11:
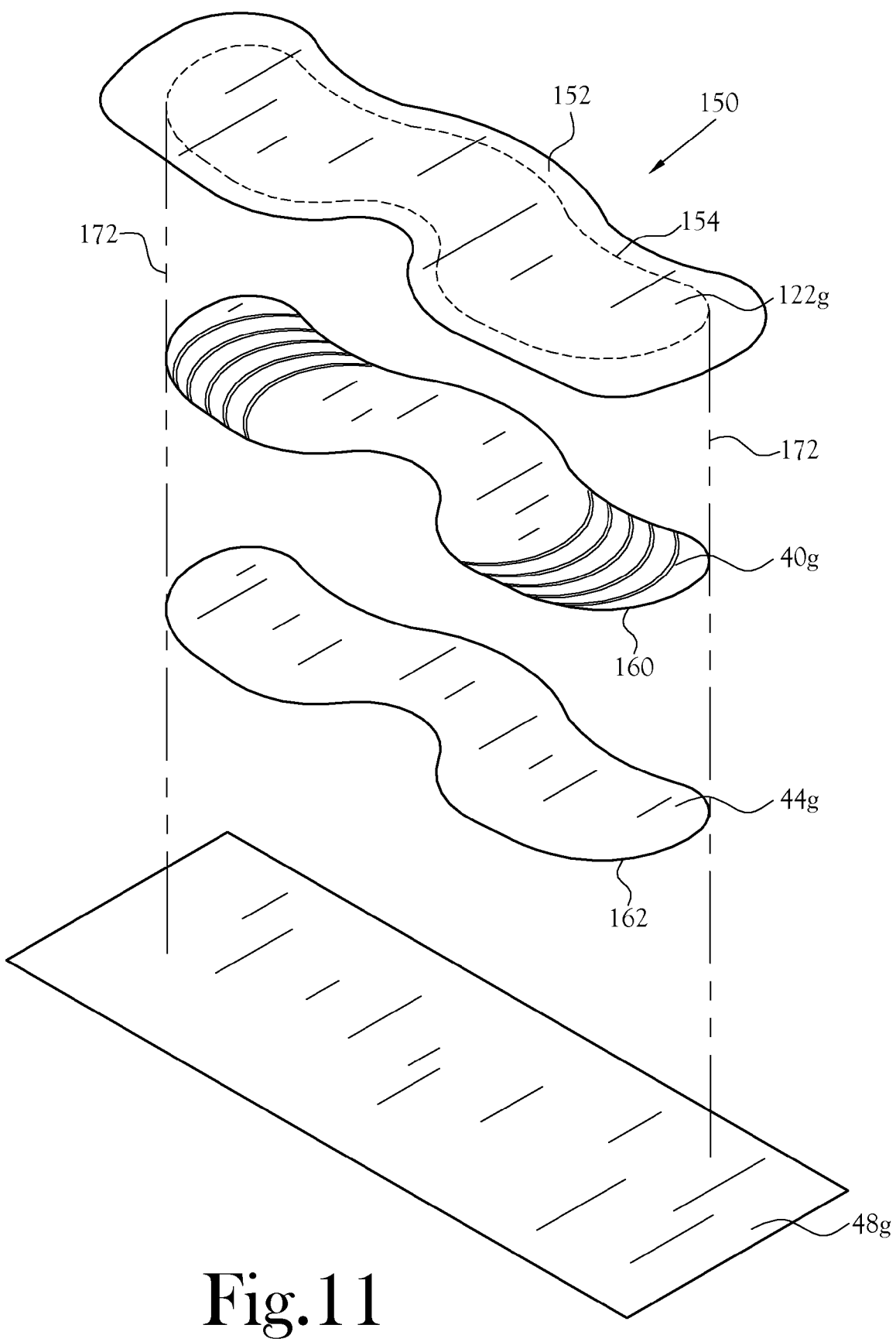
FIG. 11 is an exploded view of an embodiment of the external nasal dilator comprising an additional layer (i.e., sheet of adhesive tape) and an instant tack surface.

FIG. 11 is an exploded view of another embodiment 150 having the fourth layer, i.e., the sheet of adhesive tape. In this embodiment 150, only the resilient sheet 40g and the adhesive layer 44g are essentially congruent, i.e., at least nearly identical in size and shape. The sheet of adhesive tape 122g has essentially the same shape, but it is larger than the resilient sheet 40g or the adhesive layer 44g. Accordingly, as shown in FIG. 11, when the sheet of adhesive tape 122g is superimposed on the resilient sheet 40g and the adhesive layer 44g, a border 152 is defined on the sheet of adhesive tape 122g. The border 152 is delimited by hidden line 154, which corresponds to the perimeter 160 of the resilient sheet 40g and the perimeter 162 of the adhesive layer 44g, as indicated by phantom lines 172. Upon application of embodiment 150 to the wearer's nose, the border 152 of the sheet of adhesive tape 122g contacts the surface of the nose, as does the adhesive layer 44g. The adhesive layer 44g, which usually comprises a hydrocolloid, does not instantaneously adhere to the wearer's nose. Body heat radiated by the wearer assists in activating the adhesive layer 44g, which becomes fully effective shortly after application to the nose. However, the border 152 of the sheet of adhesive tape 122g usually comprises an acrylic adhesive, which causes the border 152 to adhere essentially instantaneously to the wearer's nose, securing the embodiment 150 in proper position at least until the adhesive layer 44g is fully activated. Thus, the border 152 operates as an "instant tack surface" 154. Finally, the adhesive-protecting sheet 48g may have any shape and size, provided it 48g at least essentially covers the adhesive layer 44g and the border 152, thereby protecting them until the embodiment 150 is applied to the wearer's nose.

Figure 12:
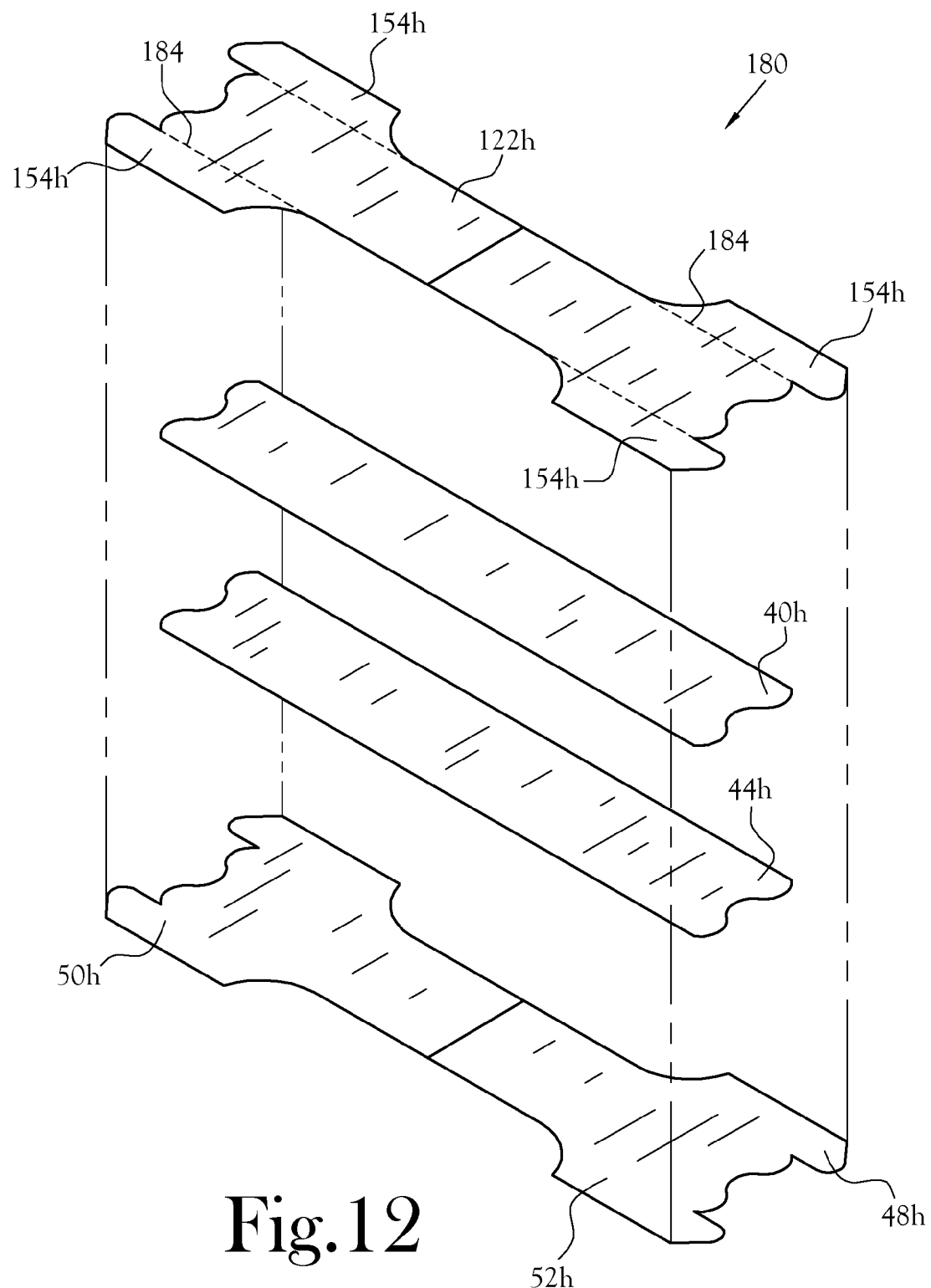
FIG. 12 is an exploded view of an embodiment of the external nasal dilator comprising an additional layer (i.e., sheet of adhesive tape) and a discontinuous instant tack surface.

FIG. 12 is an exploded view of another embodiment 180 having the fourth layer, i.e., the sheet of an adhesive tape. This embodiment 180 is analogous in many respects to embodiment 150, which is shown in FIG. 11 and described in the previous paragraph. In this embodiment 180, the resilient sheet 40h and the adhesive layer 44h are congruent, and the resilient sheet 40h is superimposed on the adhesive layer 44h. The sheet of adhesive tape 122h is superimposed on the resilient sheet 40h, essentially covering it 40h. However, the area of the sheet of adhesive tape 122h is greater than the area of the resilient sheet 40h (or the adhesive layer 44h), which, in this embodiment, results in an "instant tack surface" 154h that is discontinuous and delimited by dotted lines 184. Additionally, the sheet of adhesive tape 122h and the adhesive-protecting sheet 48h are congruent. The latter 48h is divided equally along its latitudinal axis into a first section 50h and a second section 52h, to facilitate its 48h removal immediately prior to application.

Figure 13:
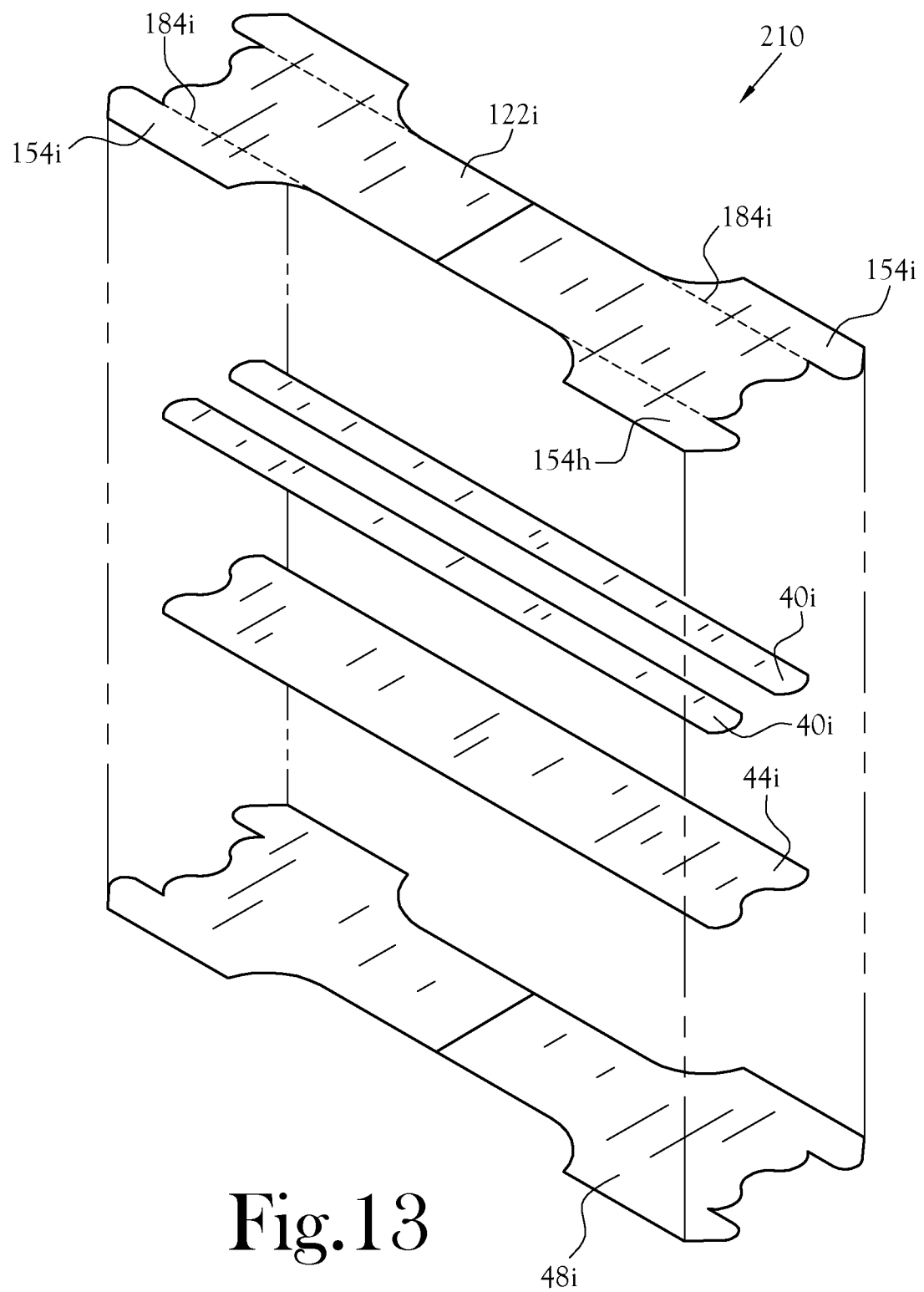
FIG. 13 is an exploded view of an embodiment of the external nasal dilator comprising an additional layer (i.e., sheet of adhesive tape), a discontinuous instant tack surface, and a discontinuous adhesive layer.
Figure 14:
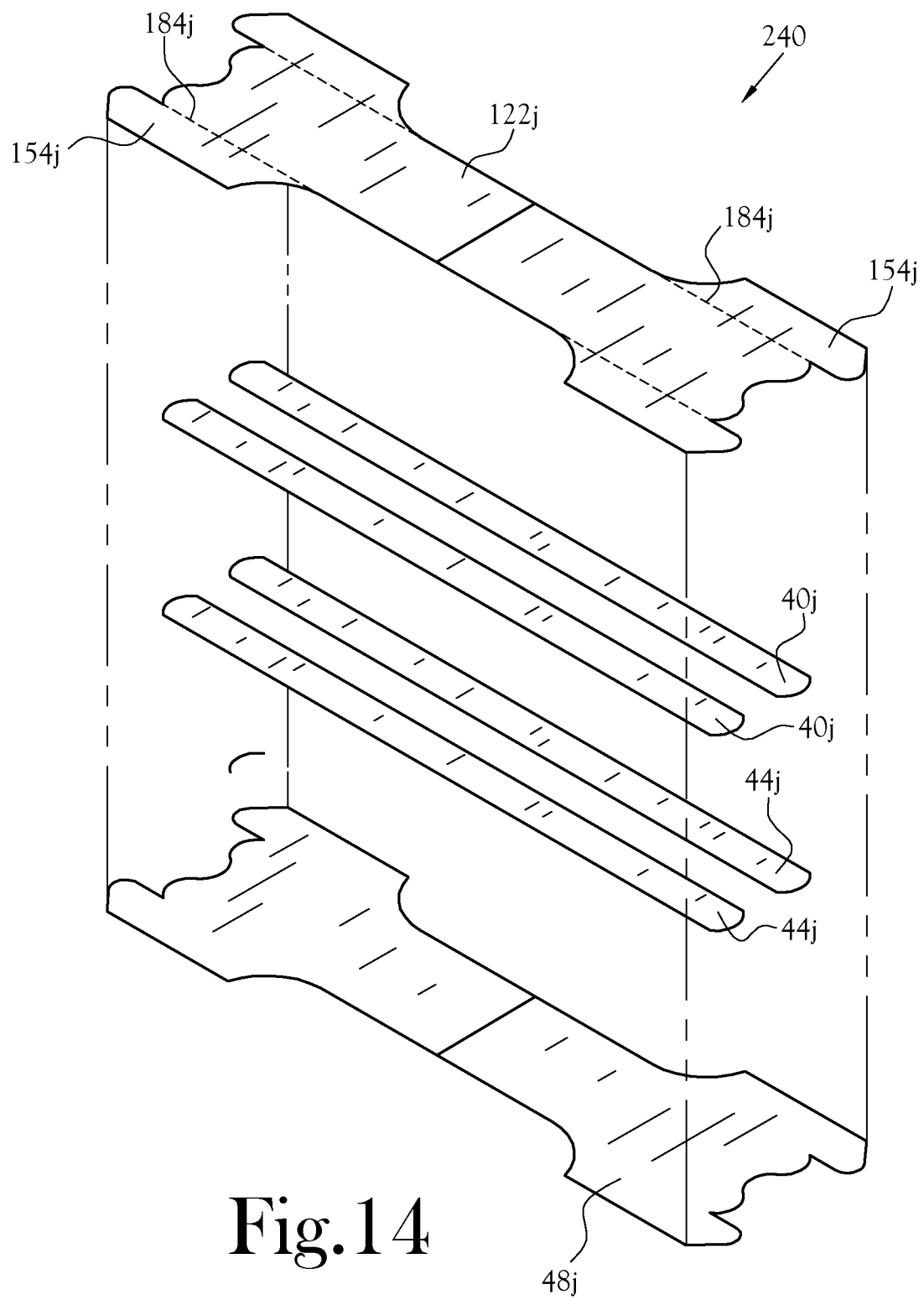
FIG. 14 is an exploded view of an embodiment of an external nasal dilator comprising an additional layer (i.e., sheet of adhesive tape), a discontinuous instant tack surface, a discontinuous resilient sheet, and a discontinuous adhesive layer.

FIG. 13 is an exploded view of still another embodiment 210 having an instant tack surface. This embodiment 210 is analogous in many respects to embodiment 180, which is shown in FIG. 12 and described in the previous paragraph. In this embodiment 210, the resilient sheet 40i and the adhesive layer 44i are not congruent, although the resilient sheet 40i is still superimposed on the adhesive layer 44i. The hallmark of this embodiment 210 is that the resilient sheet 40i is discontinuous. In some instances, this enables the peel forces to be managed more effectively, including instances in which, for the purpose of reducing peel forces, it is imprudent or impractical (1) to reduce further the thickness of the resilient sheet or (2) to etch or impress more or deeper grooves in the resilient sheet. The "instant tack surface" 154i defined by the sheet of adhesive tape 122i is discontinuous and delimited by dotted lines 184i. As in the previous embodiment 180, the sheet of adhesive tape 122i and the adhesive-protecting sheet 48i are congruent. FIG. 14 is an exploded view of still another embodiment 240 having an "instant tack surface." In this embodiment 240, the resilient sheet 40j and the adhesive layer 44j are congruent and both are discontinuous. The "instant tack surface" 154j is discontinuous and delimited by dotted lines 184j. As in the previous embodiment 210, the "instant tack surface" 154j defined by the sheet of adhesive tape 122j is discontinuous and delimited by dotted lines 184j. Again, the sheet of adhesive tape 122j and the adhesive-protecting sheet 48j are congruent.

At least some of the embodiments of the nasal dilator disclosed herein are amenable to continuous and automated manufacture. In one embodiment of the method of making the present invention, a roll of a three-layered material is provided. The three layers of the three-layered material consist respectively of (1) a resilient sheet, (2) an adhesive-protecting sheet, and (3) an adhesive layer (hydrocolloid in this instance) between the resilient sheet and the adhesive-protecting material. The three-layered material is drawn into a first set of rollers, one of which is a die that impresses the first surface of the resilient sheet (i.e., the surface opposite the adhesive layer) to form grooves in that first surface. ("Die" as used herein is intended to have a broad meaning that includes, but is not limited to, the following: rotary die, laser die, flatbed die, and stamping die.) The three-layered material, after exiting the first set of rollers, is drawn into a second set of rollers, one of which is a die that sections, from the three-layered material, pieces having the perimeter (overall) shape of the dilator of the present invention, thereby essentially yielding the dilator of the present invention (e.g., embodiments 10 and 90). Simultaneously, the roller opposite the die "kiss cuts" the adhesive-protecting sheet such that it is divided equally along its latitudinal axis to facilitate its removal immediately prior to application to the nose. Finally, any extraneous three-layered material is drawn into a third roller ("waste" roller) to facilitate disposal.

Another embodiment of the method of making the present invention (e.g., embodiments 10 and 90) also uses the roll of three-layered material described in the previous paragraph. In this embodiment, the three-layered material is drawn into the first set of rollers, one of which is a die impresses grooves into the second surface of the resilient sheet (i.e., the surface that is contacting the adhesive layer) by penetrating both the adhesive-protecting sheet and the adhesive layer. Thereafter, the three-layered material is drawn into a second set of rollers, where the now-perforated adhesive-protecting sheet is removed and stored on a roller for later disposal. Next, the remaining material, which now consists of two layers, is drawn into a third set of rollers, where a new adhesive-protecting sheet is added. This three-layered material, after exiting the third set of rollers, is drawn into a fourth set of rollers, one of which is a die that sections, from the three-layered material, pieces having the perimeter (overall) shape of the external nasal dilator, thereby essentially yielding the dilator of the present invention. Simultaneously, the roller opposite the die "kiss cuts" the adhesive-protecting sheet such that it is divided equally along its latitudinal axis to facilitate its removal immediately prior to application to the nose. Finally, any extraneous three-layered material is drawn into a third roller ("waste" roller) to facilitate disposal.

The third embodiment of the method of making the present invention uses a different starting material. The hallmark of this embodiment is that (1) a roll of resilient material (e.g., PETG) is provided in an unlaminated state, i.e., neither of its surfaces is coated with a substance (e.g., an adhesive) and (2) grooves are impressed (e.g., kiss-cut) upon the second surface of the resilient material prior to the application of an adhesive (e.g., hydrocolloid) to that second surface. The resilient material (or resilient sheet) is drawn into a first set of rollers, one of which is a die that impresses the second surface of the resilient sheet, yielding grooves in that second surface. Next, the resilient sheet is drawn into a second set of rollers, where it is merged with a two-layered material consisting of an adhesive layer (hydrocolloid in this instance) and an adhesive-protecting sheet. Thereafter, this three-layered material is drawn into a third set of rollers, where it is heated to encourage bonding between the resilient sheet and the adhesive layer. The three-layered material, after exiting the third set of rollers, is drawn into a fourth set of rollers, one of which is a die that sections, from the three-layered material, pieces having the perimeter (overall) shape of the dilator of the present invention, thereby essentially yielding the dilator of the present invention. Simultaneously, the roller opposite the die "kiss cuts" the adhesive-protecting sheet such it is divided equally along its latitudinal axis to facilitate removal of the liner immediately prior to application of the dilator to the nose. Finally, any extraneous three-layered material is drawn onto a roller to facilitate disposal.

The methods of making disclosed herein pertain to nasal dilators having three layers (e.g., embodiments 10 and 90). It will now be apparent to those skilled in that art that these methods can be modified to produce a nasal dilator having four layers (e.g., embodiments 120, 150, and 180). More generally, it will also be apparent to those skilled in the art that the grooves can be etched (instead of impressed) into the resilient sheet and that etching may be advantageous in some circumstances.

While the present invention has been illustrated by description of several embodiments and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An external nasal dilator comprising:
a bridge region for primarily contacting a bridge of a nose;
a first nasal passage region, adjacent to the bridge region, for primarily contacting a first side of the nose;
a second nasal passage region, adjacent to the bridge region and distal to the first nasal passage region, for primarily contacting a second side of the nose;
a first end region adjacent to the first nasal passage region and distal to the bridge region; and
a second end region adjacent to the second nasal passage region and distal to the bridge region;
wherein the first nasal passage region has an average width that is substantially less than the average width of the bridge region; and
further comprising an adhesive layer defining a first major surface and a second major surface;
a resilient sheet, defining a third major surface and a fourth major surface, the third major surface and the fourth major surface terminating at a first edge and at a second edge opposite the first edge forming a first direction between the first edge and the second edge, the resilient sheet being superposed on the adhesive layer such that the fourth major surface contacts the first major surface, wherein the third major surface, the fourth major surface, or both comprise multiple grooves beginning at the first edge and terminating at the second edge at least one groove extending across each of the first end region and the second end region and at least one groove extending across each of the first nasal passage region and the second nasal passage region, which when the resilient sheet is in a planar orientation, the groove is curved along the first direction; and
an adhesive-protecting sheet, defining a fifth major surface and a sixth major surface, superposed on the adhesive layer such that the fifth major surface contacts the second major surface, wherein the adhesive-protecting sheet comprises a first material suitable for protecting the adhesive layer and for being removably adhered to the adhesive layer.

2. The external nasal dilator of claim 1, wherein the third major surface comprises at least one curved groove.

3. The external nasal dilator of claim 1, wherein the fourth major surface comprises at least one curved groove.

4. The external nasal dilator of claim 1, wherein the adhesive layer comprises a hydrocolloid.

5. The external nasal dilator of claim 1, wherein the resilient material is selected from the group consisting of PET, boPET, PETG, HDPE, and polyester.

6. The external nasal dilator of claim 1, wherein the first material is selected from the group consisting of polypropylene, a similar thermoplastic resin, and a paper-based material.

7. The external nasal dilator of claim 1, further comprising a sheet of adhesive tape superposed on the resilient sheet such that the sheet of adhesive tape adheres to the third major surface.

* * * * *